US006593273B2

(12) United States Patent
Asrar et al.

(10) Patent No.: US 6,593,273 B2
(45) Date of Patent: Jul. 15, 2003

(54) METHOD FOR REDUCING PEST DAMAGE TO CORN BY TREATING TRANSGENIC CORN SEEDS WITH PESTICIDE

(75) Inventors: Jawed Asrar, Chesterfield, MO (US); Frank C. Kohn, St. Louis, MO (US); Ernest F. Sanders, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 09/968,422

(22) Filed: Oct. 1, 2001

(65) Prior Publication Data

US 2003/0018992 A1 Jan. 23, 2003

Related U.S. Application Data

(60) Provisional application No. 60/238,406, filed on Oct. 6, 2000.

(51) Int. Cl.[7] .............................. A01N 25/26; A01H 5/00
(52) U.S. Cl. ..................... 504/100; 800/300.1; 800/302
(58) Field of Search ...................... 504/100; 800/300.1, 800/302

(56) References Cited

U.S. PATENT DOCUMENTS

| | | | |
|---|---|---|---|
| 4,245,432 A | 1/1981 | Dannelly | 47/57.6 |
| 4,272,417 A | 6/1981 | Barke et al. | 260/22 R |
| 4,339,456 A | 7/1982 | Rushing | 424/274 |
| 4,372,080 A | 2/1983 | Rushing | 47/57.6 |
| 4,383,391 A | 5/1983 | Thomas et al. | 47/57.6 |
| 4,634,587 A | 1/1987 | Hsiao | 424/19 |
| 4,735,015 A | 4/1988 | Schmolka | 47/57.6 |
| 4,766,203 A | 8/1988 | Krieg et al. | 530/370 |
| 4,797,279 A | 1/1989 | Karamata et al. | 424/93 |
| 4,910,016 A | 3/1990 | Gaertner et al. | 424/93 |
| 5,187,091 A | 2/1993 | Donovan et al. | 435/240.4 |
| 5,264,364 A | 11/1993 | Donovan et al. | 435/252.5 |
| 5,300,127 A | 4/1994 | Williams | 47/57.6 |
| 5,328,942 A | 7/1994 | Akhtar et al. | 524/35 |
| 5,378,625 A | 1/1995 | Donovan et al. | 435/252.5 |
| 5,382,429 A | 1/1995 | Donovan et al. | 424/93.461 |
| 5,427,786 A | 6/1995 | Payne et al. | 424/93.461 |
| 5,446,019 A | 8/1995 | Ely et al. | 514/2 |
| 5,580,544 A | 12/1996 | Dao et al. | 424/43 |
| 5,622,003 A | 4/1997 | Narayanan | 47/57.6 |
| 5,625,136 A | 4/1997 | Koziel et al. | 800/205 |
| 5,629,469 A | 5/1997 | Deluca-Flaherty et al. | 800/205 |
| 5,661,103 A | 8/1997 | Harms et al. | 504/147 |
| 5,696,144 A | 12/1997 | Royalty et al. | 514/404 |
| 5,770,695 A | 6/1998 | Payne et al. | 530/350 |
| 5,791,084 A | 8/1998 | Kohno et al. | 47/57.6 |
| 5,834,447 A | 11/1998 | Phillion et al. | 514/63 |
| 5,849,320 A | 12/1998 | Turnblad et al. | 424/410 |
| 5,859,336 A | 1/1999 | Koziel et al. | 800/205 |
| 5,876,739 A | 3/1999 | Turnblad et al. | 424/408 |
| 5,877,012 A | 3/1999 | Estruch et al. | 435/252.3 |
| 5,882,713 A | 3/1999 | Eskins et al. | 426/578 |
| 5,939,356 A | 8/1999 | Wellinghoff | 504/100 |
| 5,952,358 A | 9/1999 | Meunier et al. | 514/357 |
| 6,023,013 A | 2/2000 | English et al. | 800/302 |
| 6,060,594 A | 5/2000 | English et al. | 536/23.71 |
| 6,063,597 A | 5/2000 | English et al. | 435/69.1 |
| 6,071,511 A | 6/2000 | Payne et al. | 424/93.2 |
| 6,093,695 A | 7/2000 | Rupar et al. | 514/12 |
| 6,331,531 B1 | 12/2001 | Kern | 514/93 |

FOREIGN PATENT DOCUMENTS

| | | | |
|---|---|---|---|
| WO | WO 97/07089 | 2/1997 | |
| WO | WO 99/09830 | 3/1999 | .......... A01N/47/24 |
| WO | WO 99/31248 | 6/1999 | |
| WO | WO 99/33343 | 7/1999 | .......... A01N/43/00 |
| WO | WO 99/35910 | 7/1999 | .......... A01N/63/00 |
| WO | 9935913 | * 7/1999 | |
| WO | WO 99/63829 | 12/1999 | .......... A01N/63/00 |
| WO | WO 00/08936 | 2/2000 | .......... A01N/57/20 |
| WO | WO 00/35277 | 6/2000 | .......... A01N/25/10 |
| WO | WO 00/35377 | 6/2000 | ............. A61F/2/06 |
| WO | WO 01/08490 | 2/2001 | .......... A01N/53/00 |

OTHER PUBLICATIONS

*Corn Rootworms*, Field Crops Pest Management Circular #16, Ohio Pest Management & Survey Program, The Ohio State University, Extension Division, Columbus, OH, Sep. 13, 2000.

Crickmore, N. et al., *Bacillus thuringiensis toxin nomenclature* (2002) http://www.biols.susx.ac.uk/Home/Neil Crickmore/Bt/index.html (Dec. 26, 2001).

Crickmore, N. et al., *Microbiology & Molecular Biology Reviews*, 62(3):807—813 (1998).

Int'l. Search Report for Ser. No. PCT/US01/30792 dated Apr. 22, 2002.

Int'l. Search Report for Ser. No. PCT/US01/42461 dated Apr. 22, 2002.

* cited by examiner

Primary Examiner—Alton N. Pryor
(74) Attorney, Agent, or Firm—Nelson, Mullins, Riley & Scarborough, LLP

(57) ABSTRACT

A method to protect corn against feeding damage by one or more pests includes the treatment of corn seed having a transgenic event that is targeted against at least one of the pests with a pesticide in an amount that is effective against the same or another of the one or more pests. Seeds having such protection are also disclosed.

46 Claims, No Drawings

METHOD FOR REDUCING PEST DAMAGE TO CORN BY TREATING TRANSGENIC CORN SEEDS WITH PESTICIDE

CROSS-REFERENCES TO RELATED APPLICATIONS

This application is a non-provisional of U.S. Patent Application No. 60/238,406, filed Oct. 6, 2000, and claims priority thereto.

BACKGROUND OF THE INVENTION (1) Field of the Invention

The present invention relates generally to the control of pests that cause damage to corn plants by their feeding activities, and more particularly to the control of such corn plant pests by the combination of a corn seed having a transgenic event and the treatment of such seed with a pesticide prior to planting the seed.

(2) Description of the Related Art

Insects and related arthropods annually destroy an estimated 15% of agricultural crops in the United States and even more than that in developing countries. In addition, competing weeds and parasitic and saprophytic plants account for even more potential yield losses.

Some of this damage occurs in the soil when plant pathogens, insects and other such soil borne pests attack the seed after planting. In the production of corn, much of the rest of the damage is caused by rootworms—insect pests that feed upon or otherwise damage the plant roots; and by cutworms, European corn borers, and other pests that feed upon or damage the above ground parts of the plant. General descriptions of the type and mechanisms of attack of pests on agricultural crops are provided by, for example, Metcalf, in *Destructive and Useful Insects*, (1962); and Agrios, in *Plant Pathology*, 3rd Ed., Academic Press (1988).

Corn is the most important grain crop in the Midwestern United States. Among the most serious insect pests of corn in this region is the larval form of three species of Diabrotica beetles. These include the Western corn rootworm, *Diabrotica vergifera vergifera* LeConte, the Northern corn rootworm, *Diabrotica berberi* Smith and *Diabrotica berberi* Lawrence, and the Southern corn rootworm, *Diabrotica undecimpunctata* howardi Barber. In fact, more insecticide is used for the control of corn rootworm than for any other pest of corn, and the total acreage treated is greater than for any other pest in the United States.

Corn rootworms (CRW) overwinter in the egg stage in fields where corn was grown the previous season. The eggs hatch from late May through June. If a corn crop is not followed by another corn crop in the subsequent year, the larvae will die. Accordingly, the impact of corn rootworm is felt most directly in areas where corn is systematically followed by corn, as is typical in many areas of the Midwestern United States.

After hatching, the larvae pass through three larval stages or instars, during which they feed on the corn root system. About three weeks is required for completion of the larval stage. Damage to the corn root system caused by the feeding of larvae is the major cause of harvest losses in corn due to corn rootworm. Corn plants that fall over and lodge in the field after weakening or destruction of a major part of the root system are the cause of a major portion of this loss, since this lodged corn cannot be harvested by conventional mechanized machinery and is left in the field.

Following completion of larval development, the larvae transform into immobile pupae, and thence into the adult beetles that emerge from the soil throughout the summer, with the period of emergence depending upon the growing location. After emergence, the adult beetles feed for about two weeks before the females start laying eggs. Initially, the adults feed predominantly in the same field from which they emerged, but later will migrate to other fields. Peak adult activity normally occurs in the U.S. Corn Belt during late July or early August in fields planted to continuous corn, but activity may peak later in first year or late maturing cornfields. Rootworm beetles begin depositing eggs in cornfields approximately two weeks after they emerge. (For more information, see, e.g., *Corn Rootworms*, Field Crops Pest Management Circular #16, Ohio Pest Management & Survey Program, The Ohio State University, Extension Division, Columbus, Ohio.; available online at www.ag.ohio-state.edu/~ohioline/icm-fact/fc-16.html, Sep. 13, 2000; and McGahen et al., *Corn Insect Control: Corn Rootworm*, PENpages number 08801502, Factsheet available from Pennsylvania State University, State College, Pa., 1989).

In present conventional agricultural practice, in cases where corn follows corn, it is normal for an insecticide to be applied to protect the corn root system from severe feeding by rootworm larvae. Conventional practice is to treat for the adult beetles or to treat for the larvae. Examples of conventional treatment formulations for adult beetles include the application of carbaryl insecticides (e.g., SEVIN® 80S at 1.0–2.0 lbs active/acre); fenvalerate or esfenvalerate (e.g., PYDRIN® 2.4EC at 0.1 to 0.2 lbs active/acre, or ASANA® 0.66EC at 0.03 to 0.05 lbs active/acre); malathion (57% E at 0.9 lbs active/acre); permethrin (e.g., AMBUSH® 2.0EC at 0.1 to 0.2 lbs active/acre, or POUNCE® 3.2EC at 0.1 to 0.2 lbs active ingredient/acre); or PENNCAP-M® at 0.25–0.5 lbs active/acre.

To treat for CRW larvae, conventional practice is to apply a soil insecticide either at or after planting, but preferably as close to egg hatching as possible. Conventional treatments include carbofuran insecticides (e.g., FURADAN® 15G at 8 oz/1000 ft of row); chloropyrifos (e.g., LORSBAN® 15G at 8 oz/1000 ft of row); fonophos (e.g., DYFONATE® 20G at 4.5 to 6.0 oz/1000 ft of row); phorate (e.g., THIMET® 20G at 6 oz/1000 ft of row); terbufos (e.g., COUNTER® 15G at 8 oz/1000 ft of row); or tefluthrin (e.g., FORCE® 3G at 4 to 5 oz/1000 ft of row).

Many of the chemical pesticides listed above are known to be harmful to humans and to animals in general. The environmental harm that these pesticides cause is often exacerbated due to the practice of applying the pesticides by foliar spraying or direct application to the surface of the soil. Wind-drift, leaching, and runoff can cause the migration of a large fraction of the pesticide out of the desired zone of activity and into surface waters and direct contact with birds, animals and humans.

Because of concern about the impact of chemical pesticides on public health and the health of the environment, significant efforts have been made to find ways to reduce the amount of chemical pesticides that are used. Recently, much of this effort has focused on the development of transgenic crops that are engineered to express insect toxicants derived from microorganisms. For example, U.S. Pat. No. 5,877,012 to Estruch et al. discloses the cloning and expression of proteins from such organisms as Bacillus, Pseudomonas, Clavibacter and Rhizobium into plants to obtain transgenic plants with resistance to such pests as black cutworms, armyworms, several borers and other insect pests. Publication WO/EP97/07089 by Privalle et al. teaches the transformation of monocotyledons, such as corn, with a recombinant DNA sequence encoding peroxidase for the protection of the plant from feeding by corn borers, earworms and cutworms. Jansens et al., in *Crop Sci.,* 37(5):1616–1624 (1997), reported the production of transgenic corn containing a gene encoding a crystalline protein from *Bacillus thuringiensis* (Bt) that controlled both generations of the European corn borer. U.S. Pat. Nos. 5,625,136 and 5,859,336 to Koziel et al. reported that the transformation of corn with a gene from *B. thuringiensis* that encoded for delta-endotoxins provided the transgenic corn with improved resistance to European corn borer. A comprehensive report of field trials of transgenic corn that expresses an insecticidal protein from *B. thuringiensis* has been provided by Armstrong et al,, in *Crop Science,* 35(2):550–557 (1995).

It was known that wild-type Bt δ-endotoxins had low activity against coleopteran insects, and Kreig et al., in 1983, reported the first isolation of a coleopteran-toxic *B. thuringiensis* strain. (See U.S. Pat. No. 4,766,203). U.S. Pat. Nos. 4,797,279 and 4,910,016, also disclosed wild-type and hybrid *B. thuringiensis* strains that produced proteins having some coleopteran activity. More recently, however, more precise genetic engineering methods have shown promise in developing modified *B. thuringiensis* proteins that have significantly higher levels of corn rootworm activity than those produced by wild-type parents. (See, e.g., WO 99/31248 to Ecogen, Inc. and Monsanto Company).

However, it is not known at present whether any transgenic event alone will be sufficiently effective to protect corn from damage by corn rootworm in heavily infested fields that are dedicated to serial corn. In fact, the total control of corn rootworm damage by any one transgenic event may not be desirable in the long term, because of the potential for the development of resistant strains of the target pest.

Another alternative to the conventional forms of pesticide application is the treatment of plant seeds with pesticides. The use of fungicides to protect seeds from attack after planting, and the use of low levels of insecticides for the protection of, for example, corn seed from wireworm, has been used for some time. Seed treatment with pesticides has the advantages providing for the protection of the seeds, while minimizing the amount of pesticide that was required and limiting the amount of contact with the pesticide and the number of different field applications that were necessary.

Other examples of the control of pests by applying insecticides directly to plant seed are provided in, for example, U.S. Pat. No. 5,696,144, which discloses that the European corn borer caused less feeding damage to corn plants grown from seed treated with a 1-arylpyrazole compound at a rate of 500 g per quintal of seed than control plants grown from untreated seed. In addition, U.S. Pat. No. 5,876,739 to Turnblad et al. (and its parent, U.S. Pat. No. 5,849,320) disclose a method for controlling soil-borne insects which involves treating seeds with a coating containing one or more polymeric binders and an insecticide. This reference provides a list of insecticides that it identifies as candidates for use in this coating and also names a number of potential target insects. However, while the U.S. Pat. No. 5,876,739 states that treating corn seed with a coating containing a particular insecticide protects corn roots from damage by the corn rootworm, it does not indicate or otherwise suggest that such treatment could be used with seed having a transgenic event.

The treatment of seed having a transgenic event with nitroimino- or nitroguanidino-compound pesticides has been mentioned (See, e.g., WO 99/35913), however, no guidance has been found as to the potential utility or efficacy of such treatments, or the details of how such treatments might be effected—such as the amounts of active ingredient that would be necessary per unit amount of seed—and no examples that would give reason to believe that the proposed treatments would actually provide suitable protection.

Therefore, although recent developments in genetic engineering of plants have improved the ability to protect plants from pests without using chemical pesticides, and while such techniques as the treatment of seeds with pesticides have reducing the harmful effects of pesticides on the environment, numerous problems remain that limit the successful application of these methods under actual field conditions. Accordingly, it would be useful to provide an improved method for the protection of plants, especially corn plants, from feeding damage by pests. It would be particularly useful if such method would reduce the required application rate of conventional chemical pesticides, and also if it would limit the number of separate field operations that were required for crop planting and cultivation.

BRIEF SUMMARY OF THE INVENTION

Briefly, therefore, the present invention is directed to a novel method for protecting a transgenic corn plant against feeding damage by one or more pests, the method comprising providing a seed for the transgenic corn plant which seed comprises a transgenic event having activity against at least one of the one or more pests; and treating the seed with an effective amount of a pesticide.

The present invention is also directed to a novel seed of a transgenic corn plant that provides increased resistance to the resulting corn plant against feeding damage by one or more pests, comprising a transgenic event having activity against at least one of the one or more pests, which seed has been treated with an effective amount of a pesticide.

The present invention is also directed to a novel transgenic corn seed that has been treated by the method of the present invention.

Among the several advantages found to be achieved by the present invention, therefore, may be noted the provision of an improved method for the protection of plants, especially corn plants, from feeding damage by pests; the provision of such a method that would reduce the required application rate of conventional chemical pesticides; and also the provision of such a method that would limit the number of separate field operations that were required for crop planting and cultivation.

DETAILED DESCRIPTION OF THE INVENTION

In accordance with the present invention, it has been discovered that corn plants can be protected against feeding damage by one or more pests by a method that includes providing a corn seed having a transgenic event that has activity against at least one of the pests and then treating the transgenic corn seed with an effective amount of a pesticide. In preferred embodiments of this invention, it has been found that the combination of a transgenic event having activity against corn rootworm and treatment of the seed with certain pesticides provides unexpectedly synergistic advantages to seeds having such treatment, including unexpectedly superior efficacy for protection against damage to the resulting corn plant by corn rootworm. In particular, it was found that corn seeds having a transgenic event that caused the production of CryBb.11231 endotoxin in combination with the treatment of such seeds with imidacloprid was unexpectedly superior to either the transgenic event alone, or to treatment with imidacloprid alone, in protecting resulting corn plants against more severe levels of damage by corn rootworm—levels of damage that are known to reduce corn yield.

Corn plants and seeds that have been engineered to include exogenous genes derived from *Bacillus thuringiensis* that encode for the expression of Cry3 δ-endotoxins having activity against Coleopteran pests are known, as are methods for the treatment of seeds (even some transgenic seeds) with pesticides. However, it had not been realized until the present invention that certain effective amounts of certain pesticides could be used to treat corn seeds having such Cry3 events, with the result that the combination would be effective, and preferably unexpectedly superior, in increasing the efficacy of both the pesticide and the transgenic event, and would provide the additional advantages of increasing the ability to match pesticidal activity against pest pressure, decreasing cost of treatment and/or application, increasing safety of seed handling, and decreasing environmental impact of either or both the event and the pesticide.

In particular, it has been found in preferred embodiments that the treatment of a transgenic corn seeds that are capable of expressing certain modified Cry3Bb proteins with from about 100 gm to about 400 gm of certain pesticides per 100 kg of seed provided unexpectedly superior protection against corn rootworm. In addition, it is believed that such combinations are also effective to protect the emergent corn plants against damage by black cutworm. The seeds of the present invention are also believed to have the property of decreasing the cost of pesticide use, because less of the pesticide can be used to obtain a required amount of protection than if the innovative method is not used. Moreover, because less pesticide is used and because it is applied prior to planting and without a separate field application, it is believed that the subject method is therefore safer to the operator and to the environment, and is potentially less expensive than conventional methods.

When it is said that some effects are "synergistic", it is meant to include the synergistic effects of the combination on the pesticidal activity (or efficacy) of the combination of the transgenic event and the pesticide. However, it is not intended that such synergistic effects be limited to the pesticidal activity, but that they should also include such unexpected advantages as increased scope of activity, advantageous activity profile as related to type and amount of damage reduction, decreased cost of pesticide and application, decreased pesticide distribution in the environment, decreased pesticide exposure of personnel who produce, handle and plant corn seeds, and other advantages known to those skilled in the art.

The present invention also provides an advantage of increasing the ability to match pesticidal activity against pest pressure. This refers to the ability to design the combination of the transgenic event and the pesticide treatment so that the seed or the resulting plant is provided with effective pesticidal activity during the period when feeding pressure from the target pest on the seed or plant reaches its maximum. By way of example, when a pesticide such as imidacloprid or terfluthrin is applied to a corn seed having a corn rootworm transgenic event, the pesticide can be applied in a coating designed to provide controlled release of the pesticide. The release rate can be selected so that the pesticide provides protection against such other pests as, for example, black cutworm, at the post emergence stage of corn, while the transgenic event provides corn rootworm protection at a later stage of plant development—when such protection is needed.

As used herein, the terms "pesticidal effect" and "pesticidal activity", or "activity" refer to a toxic effect against a pest. The terms "activity against (one or more) pests", also have the same meaning. When it is said that a seed or plant is "protected against feeding damage by one or more pests", it is meant that such seed or plant possesses a feature having direct or indirect action on one or more pests that results in reduced feeding damage by such pest or pests on the seeds, roots, shoots and foliage of plants having such feature as compared to the feeding damage caused under the same conditions to plants not having such feature. Such direct or indirect actions include inducing death of the pest, repelling the pest from the plant seeds, roots, shoots and/or foliage, inhibiting feeding of the pest on, or the laying of its eggs on, the plant seeds, roots, shoots and/or foliage, and inhibiting or preventing reproduction of the pest.

The term "insecticidal activity" has the same meaning as pesticidal activity, except it is limited to those instances where the pest is an insect. Except where specifically noted, when the term "pesticide" is used herein, that term refers to a chemical pesticide that is supplied externally to the seed, and it is not meant to include active agents that are produced by the particular seed or the plant that grows from the particular seed. However, the terms "pesticidal activity" and "insecticidal activity" can be used with reference to the activity of either, or both, an externally supplied pesticide and/or an agent that is produced by the seed or the plant.

One feature of the present invention is a seed of a transgenic corn plant. As used herein, the terms "transgenic corn plant" mean a corn plant or progeny thereof derived from a transformed corn plant cell or protoplast, wherein the plant DNA contains an introduced exogenous DNA molecule not originally present in a native, non-transgenic plant of the same strain.

The transgenic corn seed is one that contains an exogenous gene that encodes a pesticidal protein. Pesticidal proteins of this type are described by Schnepf et al., in *Microbiology & Molecular Biology Reviews*, 62:775–806 (1998), and by ffrench-Constant and Bowen, in *CMSL Cell. Mol. Life Sci.*, 57:828–833 (2000). In one application of the invention, the pesticidal protein is an insecticidal protein.

It is preferred that the seed contains an exogenous gene derived from a strain of *Bacillus thuringiensis*, and in particular, it is preferred that the exogenous gene is one that encodes an insecticidal δ-endotoxin derived from *B. thuringiensis*. Such δ-endotoxins are described in WO 99/31248 and U.S. Pat. No. 6,063,597, and include the Cry3 toxins. Nucleic acid segments that encode modified *B. thuringiensis* coleopteran-toxic crystal proteins that are useful in the present invention are described in U.S. Pat. No. 6,060,594, and insect resistant transgenic plants that include nucleic acid sequences that encode such insecticidal proteins are discussed in U.S. Pat. No. 6,023,013. It is preferred that the δ-endotoxins of the present invention include the Cry3B proteins, and even more preferred that the δ-endotoxins include the coleopteran-active Cry3Bb proteins. The nomenclature of the *B. thuringiensis* insecticidal crystal proteins was set forth by Hofte and Whitely, *Microbiol. Rev.*, 53:242–255, 1989. This nomenclature has been revised, and the revised nomenclature can be found at http://epunix.biols.susx.ac.uk/Home/Neil-Crickmore/Bt/index.html. The revised nomenclature will be used herein to describe transgenic event features and the δ-endotoxin proteins encoded by the transgenic event.

When the terms "transgenic event" are used herein, such terms are meant to refer to the genetically engineered DNA that is described above, but also to include the protein(s) that are encoded by the modified gene. A transgenic event in a corn seed, or corn plant, therefore, includes the ability to express a protein. When it is said that a "transgenic event has activity against a pest", it is to be understood that it is the protein that is encoded by the gene that actually has such activity when the protein is expressed and brought into contact with the pest.

WO 99/31248 and U.S. Pat. No. 6,063,597 describe methods for genetically engineering B. thuringiensis δ-endotoxin genes so that modified δ-endotoxins can be expressed. The modified δ-endotoxins differ from the wild-type proteins by having specific amino acid substitutions, additions or deletions as compared with the proteins produced by the wild-type organism. Such modified δ-endotoxins are identified herein by the use of an asterisk (*), or by reference to a specific protein by its identifying number. Thus, a genetically modified Cry3 δ-endotoxin would be expressed as Cry3*, examples of which include, without limitation: Cry3Bb.11230, Cry3Bb.11231, Cry3Bb.11232, Cry3Bb. 11233, Cry3Bb. 11234, Cry3Bb.11235, Cry3Bb. 11236, Cry3Bb. 11237, Cry3Bb. 11238, Cry3Bb.11239, Cry3Bb.11241, Cry3Bb.11242, and Cry3Bb.11098.

Some of the modified δ-endotoxins that were described in WO 99/31248 and in U.S. Pat. No. 6,063,597 were found to have enhanced activity against coleopteran insects, and in particular against Diabrotica spp., including corn rootworm. As used herein, the terms "enhanced activity" refer to the increased insecticidal activity of a modified toxin as compared with the activity of the same toxin without the amino acid modifications when both are tested under the same conditions. In particular, it was found that Cry3* δ-endotoxins had enhanced activity against corn rootworm, and are therefore preferred for use in the present invention. More preferred are Cry3B* δ-endotoxins, and even more preferred are Cry3Bb* δ-endotoxins. Even more preferred transgenic events are those that comprise the ability to express the modified δ-endotoxins that are listed in the following table. Also shown in the table are strains of transgenic B. thuringiensis that include genes for expression of the respective novel endotoxins, and the date and accession number of their deposit with the Agricultural Research Service Collection (NRRL) at 1815 N. University Street, Peoria, Ill. 91904.

| STRAIN | DEPOSIT DATE | PROTEIN | ACCESSION NUMBER (NRRL NUMBER) |
| --- | --- | --- | --- |
| EG11230 | May 27, 1997 | Cry3Bb.11230 | B-21768 |
| EG11231 | May 27, 1997 | Cry3Bb.11231 | B-21769 |
| EG11232 | May 27, 1997 | Cry3Bb.11232 | B-21770 |
| EG11233 | May 27, 1997 | Cry3Bb.11233 | B-21771 |
| EG11234 | May 27, 1997 | Cry3Bb.11234 | B-21772 |
| EG11235 | May 27, 1997 | Cry3Bb.11235 | B-21773 |
| EG11236 | May 27, 1997 | Cry3Bb.11236 | B-21774 |
| EG11237 | May 27, 1997 | Cry3Bb.11237 | B-21775 |
| EG11238 | May 27, 1997 | Cry3Bb.11238 | B-21776 |
| EG11239 | May 27, 1997 | Cry3Bb.11239 | B-21777 |
| EG11241 | May 27, 1997 | Cry3Bb.11241 | B-21778 |
| EG11242 | May 27, 1997 | Cry3Bb.11242 | B-21779 |
| EG11098 | Nov. 28, 1997 | Cry3Bb.11098 | B-21903 |

It has also been found that a preferred use of the present invention is for reducing pest feeding damage when used in combination with seeds having transgenic events that have certain levels of effectiveness against such pest. To illustrate which levels of effectiveness are preferred, the following example will use the Iowa Root Rating Method (Hills and Peters, J. Econ. Entomol., 64:764–765, 1971), which measures corn rootworm feeding damage to corn roots on a 1–6 scale. In the rating, 1=no damage or only a few minor feeding scars; 2=feeding scars evident but no roots eaten off to within 1½ inch of the plant; 3=several roots eaten off to within 1½ inch of the plant, but never the equivalent of an entire node of roots is destroyed; 4=one root node completely destroyed; 5=two root nodes completely destroyed; and 6=three or more root nodes destroyed. A destroyed root is defined as a root that has been pruned to within 1½ inch of the base. Pruned roots do not have to originate from a single node, but all pruned roots must equal the equivalent of a full node to count as a destroyed node.

As used herein, a transgenic event is within the preferred range of effectiveness level against a target pest if that event reduces feeding damage by that pest by a certain amount as compared with the same crop without the transgenic event, but does not prevent substantially all damage by the target pest. For example, if 10% of transgenic corn suffered corn rootworm damage of 4 or higher on the Iowa 1–6 Scale, while 80% of non-transgenic corn suffered damage of 4 or higher, then it could be said that the damage to the transgenic corn was (10/80)×100=12.5% of that of the non-transgenic corn. For the purposes of the present invention, it will be understood that a transgenic event in corn is within the preferred range of effectiveness level if corn having such event suffers from about 5% to about 50% of the damage suffered by non-transgenic corn due to the same pest under the same conditions. It is more preferred that corn having such transgenic event suffers from about 10% to about 40% of the damage suffered by non-transgenic corn by the same pest under the same conditions, even more preferred is damage of from about 15% to about 30%, and yet more preferred is damage of from about 20% to about 30% of the damage suffered by non-transgenic corn by the same pest under the same conditions. As used herein, when the term "about" is used to describe the degree of damage to corn, it is to be understood that the degree of damage can be above or below the limits described by as much as 1% or 2% and still be considered to be within the ranges described. By way of example, a level of 4.5% damage would be regarded as being "about 5%".

Without wishing to be bound to this or any other theory, it is believed that the pesticidal seed treatment can provide significant advantages when combined with a transgenic event that provides protection that is within the preferred effectiveness range against a target pest. In addition, it is believed that there are situations that are well known to those having skill in the art, where it is advantageous to have such transgenic events within the preferred range of effectiveness.

The present invention also includes seeds and plants having more that one transgenic event. Such combinations are referred to as "stacked" transgenic events. These stacked transgenic events can be events that are directed at the same target pest, or they can be directed at different target pests. In one preferred method, a seed having the ability to express a Cry 3 protein also has the ability to express at least one other insecticidal protein that is different from a Cry 3 protein.

In another preferred method, the seed having the ability to express a Cry 3 protein also has a transgenic event that provides herbicide tolerance. It is more preferred that the transgenic event that provides herbicide tolerance is an event that provides resistance to glyphosate, N-(phosphonomethyl) glycine, including the isopropylamine salt form of such herbicide, even more preferred is the transgenic event that is effective to provide the herbicide resistance of ROUNDUP READY® plants and seeds available from Monsanto Co., St. Louis, Mo.

In the present method, a corn seed having a transgenic event is treated with a pesticide.

Pesticides suitable for use in the invention include pyrethrins and synthetic pyrethroids; oxadizine derivatives; chloronicotinyls; nitroguanidine derivatives; triazoles; organophosphates; pyrrols; pyrazoles; phenyl pyrazoles; diacylhydrazines; biological/fermentation products; and carbamates. Further information about pesticides within these categories can be found, for example, in *The Pesticide Manual*, 11th Ed., C. D. S. Tomlin, Ed., British Crop Protection Council, Farnham, Surry, UK (1997).

Pyrethroids that are useful in the present composition include pyrethrins and synthetic pyrethroids. The pyrethrins that are preferred for use in the present method include, without limitation, 2-allyl-4-hydroxy-3-methyl-2-cyclopenten-1-one ester of 2,2-dimethyl-3-(2methyl propenyl)-cyclopropane carboxylic acid, and/or (2-methyl-1-propenyl) -2-methoxy-4-oxo-3-(2 propenyl)-2-cyclopenten-1-yl ester and mixtures of cis and trans isomers thereof (Chemical Abstracts Service Registry Number ("CAS RN") 8003-34-7).

Synthetic pyrethroids that are preferred for use in the present invention include (s)-cyano(3-phenoxyphenyl) methyl 4-chloro alpha (1-methylethyl)benzeneacetate (fenvalerate, CAS RN 51630-58-1), (S)-cyano (3-phenoxyphenyl) methyl (S)-4-chloro-alpha-(1-methylethyl) benzeneacetate (esfenvalerate, CAS RN 66230-04-4), (3-phenoxyphenyl)-methyl(+)cis-trans-3-(2,2-dichoroethenyl)-2,2-dimethylcyclopropanecarboxylate (permethrin, CAS RN 52645-53-1), (±) alpha-cyano-(3-phenoxyphenyl) methyl(+)-cis,trans-3-(2,2-dichloroethenyl)-2,2-dimethyl-cyclopropane carboxylate (cypermethrin, CAS RN 52315-07-8), (beta-cypermethrin, CAS RN 65731-84-2), (theta cypermethrin, CAS RN 71697-59-1), S-cyano (3-phenoxyphenyl) methyl (±) cis/trans 3-(2,2-dichloroethenyl) 2,2 dimethylcyclopropane carboxylate (zeta-cypermethrin, CAS RN 52315-07-8), (s)-alpha-cyano-3-phenoxybenzyl (IR,3R)-3-(2,2-dibromovinyl)-2,2-dimethyl cyclopropanecarboxylate (deltamethrin, CAS RN 52918-63-5), alpha-cyano-3-phenoxybenzyl 2,2,3,3,-tetramethyl cyclopropoanecarboxylate (fenpropathrin, CAS RN 64257-84-7), (RS)-alpha-cyano-3-phenoxybenzyl(R)-2-[2-chloro-4-(trifluoromethyl) anilino]-3-methylbutanoate (tau-fluvalinate, CAS RN 102851-06-9), (2,3,5,6-tetrafluoro-4-methylphenyl)-methyl-(1 alpha, 3 alpha)-(Z)-(±)-3-(2-chloro-3,3,3-trifluoro-1-propenyl)-2,2-dimethylcyclopropanecarboxylate (tefluthrin, CAS RN 79538-32-2), (±)-cyano (3-phenoxyphenyl) methyl (±)-4-(difluoromethoxy)-alpha-(1-methyl ethyl) benzeneacetate (flucythrinate, CAS RN 70124-77-5), cyano(4-fluoro-3-phenoxyphenyl)methyl 3-[2-chloro-2-(4-chlorophenyl)ethenyl]-2,2-dimethylcyclopropanecarboxylate (flumethrin, CAS RN 69770-45-2), cyano(4-fluoro-3-phenoxyphenyl) methyl 3-(2,2-dichloroethenyl)-2,2-dimethyl-cyclopropanedarboxylate (cyfluthrin, CAS RN 68359-37-5), (beta cyfluthrin, CAS RN 68359-37-5), (transfluthrin, CAS RN 118712-89-3), (S)-alpha-cyano-3-phenoxybenzyl(Z)-(IR-cis)-2,2-dimethyl-3-[2-(2,2,2-trifluoro-trifluoromethyl-ethoxycarbonyl)vinyl]cyclopropane carboxylate (acrinathrin, CAS RN 101007-06-1), (IR cis) S and (IS cis) R enantiomer isomer pair of alpha-cyano-3-phenoxybenzyl-3-(2,2dichlorovinyl)-2,2-dimethylcyclopropane carboxylate (alpha-cypermethrin, CAS RN 67375-30-8), [IR,3S)3(1'RS) (1',2',2',2'-tetrabromoethyl)]-2,2-dimethyl cyclopropanecarboxylic acid (s)-alpha-cyano-3-phenoxybenzyl ester (tralomethrin, CAS RN 66841-25-6), cyano-(3-phenoxyphenyl) methyl 2,2-dichloro-1-(4-ethoxyphenyl) cyclopropane carboxylate (cycloprothrin, CAS RN 63935-38-6), [1α,3α(Z)]-(±)-cyano-(3-phenoxyphenyl)methyl 3-(2-chloro-3,3,3-trifluoro-1-propenyl)-2,2-cimethylcyclopropanecarboxylate (cyhalothrin, CAS RN 68085-85-8), [1 alpha (s), 3 alpha(z)]-cyano(3-phenoxyphenyl) methyl-3-(2-chloro-3,3,3-trifluoro-1-propenyl)-2,2-dimethylcyclopropane carboxylate (lambda cyhalothrin, CAS RN 91465-08-6), (2-methyl [1,1'-biphenyl]-3-yl) methyl 3-(2-chloro-3,3,3-trifluoro-1-propenyl)-2,2-dimethyl-cyclopropanecarboxylate (bifenthrin, CAS RN 82657-04-3), 5-1-benzyl-3-furylmethyl-d-cis(1R,3S,E)2,2-dimethyl-3-(2-oxo,-2,2,4,5 tetrahydro thiophenylidenemethyl)cyclopropane carboxylate (kadethrin, RU15525, CAS RN 58769-20-3), [5-(phenyl methyl)-3-furanyl]-3-furanyl 2,2-dimethyl-3-(2-methyl-1-propenyl) cyclopropane carboxylate (resmethrin, CAS RN 10453-86-8), (1 R-trans)-[5-(phenylmethyl)-3-furanyl] methyl 2,2-dimethyl-3-(2-methyl-1 -propenyl) cyclopropanecarboxylate (bioresmethrin, CAS RN 28434-01-7), 3,4,5,6-tetra hydro-phthalimidomethyl-(IRS)-cis-trans-chrysanthemate (tetramethrin, CAS RN 7696-12-0), 3-phenoxybenzyl-d-I-cis,trans 2,2-dimethyl-3-(2-methylpropenyl) cyclopropane carboxylate (phenothrin, CAS RN 26002-80-2); (empenthrin, CAS RN 54406-48-3); (cyphenothrin; CAS RN 39515-40-7), (prallethrin, CAS RN 23031-36-9), (imiprothrin, CAS RN 72963-72-5), (RS)-3-allyl-2-methyl-4-oxcyclopent-2-enyl-(1A,3R; 1R,3S)-2,2-dimethyl-3-(2-methylprop-1-enyl) cyclopropane carboxylate (allethrin, CAS RN 584-79-2), (bioallethrin, CAS RN 584-79-2), and (ZXI8901, CAS RN 160791-64-0). It is believed that mixtures of one or more of the aforementioned synthetic pyrethroids can also be used in the present invention. Particularly preferred synthetic pyrethroids are tefluthrin, lambda cyhalothrin, bifenthrin, permethrin and cyfluthrin. Even more preferred synthetic pyrethroids are tefluthrin and lambda cyhalothrin, and yet more preferred is tefluthrin.

Insecticides that are oxadiazine derivatives are useful in the subject method. The oxadizine derivatives that are preferred for use in the present invention include 5-(2-chloropyrid-5-ylmethyl)-3-methyl-4-nitroiminoperhydro-1, 3,5-oxadiazine, 3-methyl-4-nitroimino-5-(1-oxido -3-pyridinomethyl) perhydro-1,3,5-oxadiazine, 5-(2-chloro-1-oxido-5-pyridiniomethyl)-3-methyl-4-nitroiminoperhydro-1,3,5-oxidiazine; and 3-methyl-5-(2-methylpyrid-5-ylmethyl)-4-nitroiminoperhydro-1,3,5-oxadiazine.

Chloronicotinyl insecticides are also useful in the subject method. Chloronicotinyls that are preferred for use in the subject composition include acetamiprid ((E)-N-[(6-chloro-3-pyridinyl)methyl]-N'-cyano-N-methyleneimidamide, CAS RN 135410-20-7), imidacloprid (1-[(6-chloro-3-pyridinyl)methol]-N-nitro-2-imidazolidinimime, CAS RN 138261-41-3), and nitenpyram (N-[(6-chloro-3-pyridinyl) methyl]-N-ethyl-N'-methyl-2-nitro-1,1-ethenediamine, CAS RN 120738-89-8).

Nitroguanidine insecticides are useful in the present method. Such nitroguanidines can include MTI 446 (nidinotefuran).

Pyrrols, pyrazoles and phenyl pyrazoles that are useful in the present method include those that are described in U.S. Pat. No. 5,952,358. Preferred pyrazoles include chlorfenapyr (4-bromo-2-(4-chlorophenyl)-1-ethoxymethyl-5-trifluoromethylpyrrole-3-carbonitrile, CAS RN 122453-73-0), fenpyroximate ((E)-1,1-dimethylethyl-4[[[[(1,3-dimethyl-5-phenoxy-1H-pyrazole-4-yl)methylene]amino]oxy]methyl]benzoate, CAS RN 111812-58-9), and tebufenpyrad (4-chloro-N[[4-1,1-dimethylethyl)phenyl]methyl]-3-ethyl-1-methyl-1H-pyrazole-5-carboxamide, CAS RN 119168-77-3). A preferred phenyl pyrazole is fipronil (5-amino-[2,6-dichloro-4-(trifluoromethyl)phenyl]-4-[(1R, S)-(trifluoromethyl)sulfinyl]-1H-pyrazole-3-carbonitrile, CAS RN 120068-37-3).

Diacylhydrazines that are useful in the present invention include halofenozide (4-chlorobenzoate-2-benzoyl-2-(1,1-dimethylethyl)-hydrazide, CAS RN 112226-61-6), methoxyfenozide (RH-2485; N-tert-buty-N'-(3-methoxy-o-toluoyl)-3,5-xylohydrazide, CAS RN 161050-58-4), and tebufenozide (3,5-dimethylbenzoic acid 1-(1,1-dimethylethyl)-2,(4-ethylbenzoyl)hydrazide, CAS RN 112410-23-8).

Triazoles, such as amitrole (CAS RN 61-82-5) and triazamate are useful in the method of the present invention. A preferred triazole is triazamate (ethyl [[1-[(dimethylamino)carbonyl]-3-(1,1-dimethylethyl) -1H-1,2,4-triazol-5-yl]thio]acetate, CAS RN 112143-82-5).

Biological/fermentation products, such as avermectin (abamectin, CAS RN 71751-41-2) and spinosad (XDE-105, CAS RN 131929-60-7) are useful in the present method.

Organophosphate insecticides are also useful as one of the components of the present method. Preferred organophosphate insecticides include acephate (CAS RN 30560-19-1), chlorpyrifos (CAS RN 2921-88-2), chlorpyrifos-methyl (CAS RN 5598-13-0), diazinon (CAS RN 333-41-5), fenamiphos (CAS RN 22224-92-6), and malathion (CAS RN 121-75-5).

In addition, carbamate insecticides are useful in the subject method. Preferred carbamate insecticides are aldicarb (CAS RN 116-06-3), carbaryl (CAS RN 63-25-2), carbofuran (CAS RN 1563-66-2), oxamyl (CAS RN 23135-22-0) and thiodicarb (CAS RN 59669-26-0).

When an insecticide is described herein, it is to be understood that the description is intended to include salt forms of the insecticide as well as any isomeric and/or tautomeric form of the insecticide that exhibits the same insecticidal activity as the form of the insecticide that is described.

The insecticides that are useful in the present method can be of any grade or purity that pass in the trade as such insecticide. Other materials that accompany the insecticides in commercial preparations as impurities can be tolerated in the subject methods and compositions, as long as such other materials do not destabilize the composition or significantly reduce or destroy the activity of any of the insecticide components or the transgenic event against the target pest(s). One of ordinary skill in the art of the production of insecticides can readily identify those impurities that can be tolerated and those that cannot.

It has been found that the present method is useful to protect seeds and plants against a wide array of agricultural pests, including insects, mites, fungi, yeasts, molds and bacteria.

When an insect is the target pest for the present invention, such pests include but are not limited to:
from the order Lepidoptera, for example,
Acleris spp., Adoxophyes spp., Aegeria spp., Agrotis spp., Alabama argillaceae, Amylois spp., Anticarsia gemmatalis, Archips spp, Argyrotaenia spp., Autographa spp., *Busseola fusca, Cadra cautella, Carposina nipponensis*, Chilo spp., Choristoneura spp., *Clysia ambiguella*, Cnaphalocrocis spp., Cnephasia spp., Cochylis spp., Coleophora spp., *Crocidolomia binotalis, Cryptophlebia leucotreta*, Cydia spp., Diatraea spp., *Diparopsis castanea*, Earias spp., Ephestia spp., Eucosma spp., *Eupoecilia ambiguella*, Euproctis spp., Euxoa spp., Grapholita spp., *Hedya nubiferana*, Heliothis spp., *Hellula undalis, Hyphantria cunea, Keiferia lycopersicella, Leucoptera scitella*, Lithocollethis spp., *Lobesia botrana*, Lymantria spp., Lyonetia spp., Malacosoma spp., *Mamestra brassicae, Manduca sexta*, Operophtera spp., *Ostrinia Nubilalis*, Pammene spp., Pandemis spp., *Panolis flammea, Pectinophora gossypiella, Phthorimaea operculella, Pieris rapae*, Pieris spp., *Plutella xylostella*, Prays spp., Scirpophaga spp., Sesamia spp., Sparganothis spp., Spodoptera spp., Synanthedon spp., Thaumetopoea spp., Tortrix spp., *Trichoplusia ni* and Yponomeuta spp.;

from the order Coleoptera, for example,
Agriotes spp., Anthonomus spp., *Atomaria linearis, Chaetocnema tibialis*, Cosmopolites spp., Curculio spp., Dermestes spp., Diabrotica spp., Epilachna spp., Eremnus spp., *Leptinotarsa decemlineata*, Lissorhoptrus spp., Melolontha spp., Orycaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.;

from the order Orthoptera, for example,
Blatta spp., Blattella spp., Gryllotalpa spp., *Leucophaea maderae*, Locusta spp., Periplaneta ssp., and Schistocerca spp.;

from the order Isoptera, for example,
Reticulitemes ssp;

from the order Psocoptera, for example,
Liposcelis spp.;

from the order Anoplura, for example,
Haematopinus spp., Linognathus spp., Pediculus spp., Pemphigus spp. and Phylloxera spp.;

from the order Mallophaga, for example,
Damalinea spp. and Trichodectes spp.; from the order Thysanoptera, for example,
Franklinella spp., Hercinothrips spp., Taeniothrips spp., *Thrips palmi, Thrips tabaci* and *Scirtothrips aurantii;* from the order Heteroptera, for example,
Cimex spp., *Distantiella theobroma*, Dysdercus spp., Euchistus spp., Eurygaster spp., Leptocorisa spp., Nezara spp., Piesma spp., Rhodnius spp., *Sahlbergella singularis*, Scotinophara spp. and Triatoma spp.;

from the order Homoptera, for example,
*Aleurothrixus floccosus, Aleyrodes brassicae*, Aonidiella spp., Aphididae, Aphis spp., Aspidiotus spp., *Bemisia tabaci*, Ceroplaster spp., *Chrysomphalus aonidium, Chrysomphalus dictyospermi, Coccus hesperidum*, Empoasca spp., *Eriosoma larigerum*, Erythroneura spp., Gascardia spp., Laodelphax spp., *Lacanium corni*, Lepidosaphes spp., Macrosiphus spp., Myzus spp., Nehotettix spp., Nilaparvata spp., Paratoria spp., Pemphigus spp., Planococcus spp., Pseudaulacaspis spp., Pseudococcus spp., Psylla ssp., *Pulvinaria aethiopica*, Quadraspidiotus spp., Rhopalosiphum spp., Saissetia spp., Scaphoideus spp., Schizaphis spp., Sitobion spp., *Trialeurodes vaporariorum, Trioza erytreae* and *Unaspis citri;* from the order Hymenoptera, for example,

Acromyrmex, Atta spp., Cephus spp., Diprion spp., Diprionidae, *Gilpinia polytoma*, Hoplocampa spp., Lasius sppp., *Monomorium pharaonis*, Neodiprion spp, Solenopsis spp. and Vespa ssp.;

from the order Diptera, for example,

Aedes spp., *Antherigona soccata, Bibio hortulanus, Calliphora erythrocephala*, Ceratitis spp., Chrysomyia spp., Culex spp., Cuterebra spp., Dacus spp., *Drosophila melanogaster*, Fannia spp., Gastrophilus spp., Glossina spp., Hypoderma spp., Hyppobosca spp., Liriomysa spp., Lucilia spp., Melanagromyza spp., Musca ssp., Oestrus spp., Orseolia spp., *Oscinella frit, Pegomyia hyoscyami*, Phorbia spp., *Rhagoletis pomonella*, Sciara spp., Stomoxys spp., Tabanus spp., Tannia spp. and Tipula spp., from the order Siphonaptera, for example, Ceratophyllus spp. und *Xenopsylla cheopis* and from the order Thysanura, for example,

*Lepisma saccharine.*

It has been found that the present invention is particularly effective when the insect pest is a Diabrotica spp., and especially when the pest is *Diabrotica virgifera, Diabrotica barberi*, or *Diabrotica undecimpunctata.*

Another application wherein the present invention is believed to be particularly effective is when the pesticide has activity against a weed or a parasitic or saprophytic plant and the transgenic event has activity against a member selected from the group consisting of *Diabrotica virgifera, Diabrotica barberi* and *Diabrotica undecimpunctata*. This is believed to be more preferred useful when the weed or a parasitic or saprophytic plant is the African plant known as "Striga", and even more preferred when the pesticide is ROUNDUP® (available from Monsanto Company).

In the method of the present invention, the pesticide is applied to a transgenic corn seed. Although it is believed that the present method can be applied to a transgenic corn seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. In one embodiment, for example, the treatment can be applied to seed corn that has been harvested, cleaned and dried to a moisture content below about 15% by weight. In an alternative embodiment, the seed can be one that has been dried and then primed with water and/or another material and then re-dried before or during the treatment with the pesticide. Within the limitations just described, it is believed that the treatment can be applied to the seed at any time between harvest of the seed and sowing of the seed. As used herein, the term "unsown seed" is meant to include seed at any period between the harvest of the seed and the sowing of the seed in the ground for the purpose of germination and growth of the plant.

When it is said that unsown seed is "treated" with the pesticide, such treatment is not meant to include those practices in which the pesticide is applied to the soil, rather than to the seed. For example, such treatments as the application of the pesticide in bands, "T"-bands, or in-furrow, at the same time as the seed is sowed are not considered to be included in the present invention.

The pesticide, or combination of pesticides, can be applied "neat", that is, without any diluting or additional components present. However, the pesticide is typically applied to the seeds in the form of a pesticide formulation. This formulation may contain one or more other desirable components including but not limited to liquid diluents, binders to serve as a matrix for the pesticide, fillers for protecting the seeds during stress conditions, and plasticizers to improve flexibility, adhesion and/or spreadability of the coating. In addition, for oily pesticide formulations containing little or no filler, it may be desirable to add to the formulation drying agents such as calcium carbonate, kaolin or bentonite clay, perlite, diatomaceous earth or any other adsorbent material. Use of such components in seed treatments is known in the art. See, e.g., U.S. Pat. No. 5,876,739. The skilled artisan can readily select desirable components to use in the pesticide formulation depending on the seed type to be treated and the particular pesticide that is selected. In addition, readily available commercial formulations of known pesticides may be used, as demonstrated in the examples below.

The seeds may also be treated with one or more of the following ingredients: other pesticides, including compounds which act only below the ground; fungicides, such as captan, thiram, metalaxyl, (methoxam=resolved isomer of metalaxyl), fludioxonil, oxadixyl, and isomers of each of those materials, and the like; herbicides, including compounds selected from carbamates, thiocarbamates, acetamides, triazines, dinitroanilines, glycerol ethers, pyridazinones, uracils, phenoxys, ureas, and benzoic acids; herbicidal safeners such as benzoxazine, benzhydryl derivatives, N,N-diallyl dichloroacetamide, various dihaloacyl, oxazolidinyl and thiazolidinyl compounds, ethanone, naphthalic anhydride compounds, and oxime derivatives; fertilizers; and biocontrol agents such as naturally-occurring or recombinant bacteria and fungi from the genera Rhizobium, Bacillus, Pseudomonas, Serratia, Trichoderma, Glomus, Gliocladium and mycorrhizal fungi. These ingredients may be added as a separate layer on the seed or alternatively may be added as part of the pesticide composition.

Preferably, the amount of the novel composition or other ingredients used in the seed treatment should not inhibit generation of the seed, or cause phytotoxic damage to the seed.

The pesticide formulation that is used to treat the transgenic corn seed in the present invention can be in the form of a suspension; emulsion; slurry of particles in an aqueous medium (e.g., water); wettable powder; wettable granules (dry flowable); and dry granules. If formulated as a suspension or slurry, the concentration of the active ingredient in the formulation is preferably about 0.5% to about 99% by weight (w/w), preferably 5–40%.

As mentioned above, other conventional inactive or inert ingredients can be incorporated into the formulation. Such inert ingredients include but are not limited to: conventional sticking agents, dispersing agents such as methylcellulose (Methocel A15LV or Methocel A15C, for example, serve as combined dispersant/sticking agents for use in seed treatments), polyvinyl alcohol (e.g., Elvanol 51-05), lecithin (e.g., Yelkinol P), polymeric dispersants (e.g., polyvinylpyrrolidone/vinyl acetate PVPNA S-630), thickeners (e.g., clay thickeners such as Van Gel B to improve viscosity and reduce settling of particle suspensions), emulsion stabilizers, surfactants, antifreeze compounds (e.g., urea), dyes, colorants, and the like. Further inert ingredients useful in the present invention can be found in McCutcheon's, vol. 1, *"Emulsifiers and Detergents,"* MC Publishing Company, Glen Rock, N.J., U.S.A., 1996. Additional inert ingredients useful in the present invention can be found in McCutcheon's, vol. 2, *"Functional Materials,"* MC Publishing Company, Glen Rock, N.J., U.S.A., 1996.

The pesticides and pesticide formulations of the present invention can be applied to seeds by any standard seed treatment methodology, including but not limited to mixing in a container (e.g., a bottle or bag), mechanical application, tumbling, spraying, and immersion. Any conventional active or inert material can be used for contacting seeds with pesticides according to the present invention, such as conventional film-coating materials including but not limited to water-based film coating materials such as Sepiret (Seppic, Inc., Fairfield, N.J.) and Opacoat (Berwind Pharm. Services, Westpoint, Pa.).

The subject pesticides can be applied to a seed as a component of a seed coating. Seed coating methods and compositions that are known in the art are useful when they are modified by the addition of one of the embodiments of the combination of pesticides of the present invention. Such coating methods and apparatus for their application are disclosed in, for example, U.S. Pat. Nos. 5,918,413, 5,891,246, 5,554,445, 5,389,399, 5,107,787, 5,080,925, 4,759,945 and 4,465,017. Seed coating compositions are disclosed, for example, in U.S. Pat. Nos. 5,939,356, 5,882,713, 5,876,739, 5,849,320, 5,834,447, 5,791,084, 5,661,103, 5,622,003, 5,580,544, 5,328,942, 5,300,127, 4,735,015, 4,634,587, 4,383,391, 4,372,080, 4,339,456, 4,272,417 and 4,245,432, among others.

Useful seed coatings contain one or more binders and at least one of the subject combinations of pesticides.

Binders that are useful in the present invention preferably comprise an adhesive polymer that may be natural or synthetic and is without phytotoxic effect on the seed to be coated. The binder may be selected from polyvinyl acetates; polyvinyl acetate copolymers; ethylene vinyl acetate (EVA) copolymers; polyvinyl alcohols; polyvinyl alcohol copolymers; celluloses, including ethylcelluloses, methylcelluloses, hydroxymethylcelluloses, hydroxypropylcelluloses and carboxymethylcellulose; polyvinylpyrolidones; polysaccharides, including starch, modified starch, dextrins, maltodextrins, alginate and chitosans; fats; oils; proteins, including gelatin and zeins; gum arabics; shellacs; vinylidene chloride and vinylidene chloride copolymers; calcium lignosulfonates; acrylic copolymers; polyvinylacrylates; polyethylene oxide; acrylamide polymers and copolymers; polyhydroxyethyl acrylate, methylacrylamide monomers; and polychloroprene.

It is preferred that the binder be selected so that it can serve as a matrix for the subject pesticides. While the binders disclosed above may all be useful as a matrix, the specific binder will depend upon the properties of the combination of pesticides. The term "matrix", as used herein, means a continuous solid phase of one or more binder compounds throughout which is distributed as a discontinuous phase one or more of the subject pesticides. Optionally, a filler and/or other components can also be present in the matrix. The term matrix is to be understood to include what may be viewed as a matrix system, a reservoir system or a microencapsulated system. In general, a matrix system consists of pesticides of the present invention and filler uniformly dispersed within a polymer, while a reservoir system consists of a separate phase comprising the subject pesticides, that is physically dispersed within a surrounding, rate-limiting, polymeric phase. Microencapsulation includes the coating of small particles or droplets of liquid, but also to dispersions in a solid matrix.

The amount of binder in the coating can vary, but will be in the range of about 0.01 to about 25% of the weight of the seed, more preferably from about 0.05 to about 15%, and even more preferably from about 0.1% to about 10%.

As mentioned above, the matrix can optionally include a filler. The filler can be an absorbent or an inert filler, such as are known in the art, and may include woodflours, clays, activated carbon, sugars, diatomaceous earth, cereal flours, fine-grain inorganic solids, calcium carbonate, and the like. Clays and inorganic solids, which may be used, include calcium bentonite, kaolin, china clay, talc, perlite, mica, vermiculite, silicas, quartz powder, montmorillonite and mixtures thereof. Sugars, which may be useful, include dextrin and maltodextrin. Cereal flours include wheat flour, oat flour and barley flour.

The filler is selected so that it will provide a proper microclimate for the seed, for example the filler is used to increase the loading rate of the active ingredients and to adjust the control-release of the active ingredients. The filler can aid in the production or process of coating the seed. The amount of filler can vary, but generally the weight of the filler components will be in the range of about 0.05 to about 75% of the seed weight, more preferably about 0.1 to about 50%, and even more preferably about 0.5% to 15%.

The pesticides that are useful in the coating are those pesticides that are described herein. The amount of pesticide that is used for the treatment of the seed will vary depending upon the type of seed and the type of active ingredients, but the treatment will comprise contacting the seeds with an amount of the combination of pesticides that is pesticidally effective. When insects are the target pest, that amount will be an amount of the insecticide that is insecticidally effective. As used herein, an insecticidally effective amount means that amount of insecticide that will kill insect pests in the larvae or pupal state of growth, or will consistently reduce or retard the amount of damage produced by insect pests.

In general, the amount of pesticide that is applied to the seed in the treatment will range from about 10 gm to about 2000 gm of the active ingredient of the pesticide per 100 kg of the weight of the seed. Preferably, the amount of pesticide will be within the range of about 50 gm to about 1000 gm active per 100 kg of seed, more preferably within the range of about 100 gm to about 600 gm active per 100 kg of seed, and even more preferably within the range of about 200 gm to about 500 gm of active per 100 kg of seed weight. Alternatively, it has been found to be preferred that the amount of the pesticide be over about 60 gm of the active ingredient of the pesticide per 100 kg of the seed, and more preferably over about 80 gm per 100 kg of seed.

In preferred embodiments of the present invention the transgenic event comprises the ability to express a Cry3Bb.11231 protein or a Cry3Bb.11098 protein, and the pesticide is selected from either imidacloprid or tefluthrin.

The pesticides that are used in the treatment must not inhibit germination of the seed and should be efficacious in protecting the seed and/or the plant during that time in the target insect's life cycle in which it causes injury to the seed or plant. In general, the coating will be efficacious for approximately 0 to 120 days after sowing.

The pesticides of the subject invention can be applied to the seed in the form of a coating. The use of a coating is particularly effective in accommodating high pesticidal loads, as can be required to treat typically refractory pests, such as corn rootworm, while at the same time preventing unacceptable phytotoxicity due to the increased pesticidal load.

Optionally, a plasticizer can be used in the coating formulation. Plasticizers are typically used to make the film that is formed by the coating layer more flexible, to improve adhesion and spreadability, and to improve the speed of processing. Improved film flexibility is important to minimize chipping, breakage or flaking during storage, handling or sowing processes. Many plasticizers may be used, however, useful plasticizers include polyethylene glycol, glycerol, butylbenzylphthalate, glycol benzoates and related compounds. The range of plasticizer in the coating layer will be in the range of from bout 0.1 to about 20% by weight.

When the pesticide used in the coating is an oily type formulation and little or no filler is present, it may be useful to hasten the drying process by drying the formulation. This optional step may be accomplished by means will known in the art and can include the addition of calcium carbonate, kaolin or bentonite clay, perlite, diatomaceous earth, or any absorbent material that is added preferably concurrently with the pesticidal coating layer to absorb the oil or excess moisture. The amount of calcium carbonate or related compounds necessary to effectively provide a dry coating will be in the range of about 0.5 to about 10% of the weight of the seed.

The coatings formed with the pesticide are preferably of the type that are capable of effecting a slow rate of release of the pesticide by diffusion or movement through the matrix to the surrounding medium.

In addition to the coating layer, the seed may be treated with one or more of the following ingredients: other pesticides including fungicides and herbicides; herbicidal safeners; fertilizers and/or biocontrol agents. These ingredients may be added as a separate layer or alternatively may be added in the pesticidal coating layer.

The pesticide formulation may be applied to the seeds using conventional coating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

The pesticide-treated seeds may also be enveloped with a film overcoating to protect the pesticide coating. Such overcoatings are known in the art and may be applied using conventional fluidized bed and drum film coating techniques.

In another embodiment of the present invention, a pesticide can be introduced onto or into a seed by use of solid matrix priming. For example, a quantity of the pesticide can be mixed with a solid matrix material and then the seed can be placed into contact with the solid matrix material for a period to allow the pesticide to be introduced to the seed. The seed can then optionally be separated from the solid matrix material and stored or used, or the mixture of solid matrix material plus seed can be stored or planted directly. Solid matrix materials which are useful in the present invention include polyacrylamide, starch, clay, silica, alumina, soil, sand, polyurea, polyacrylate, or any other material capable of absorbing or adsorbing the pesticide for a time and releasing that pesticide into or onto the seed. It is useful to make sure that the pesticide and the solid matrix material are compatible with each other. For example, the solid matrix material should be chosen so that it can release the pesticide at a reasonable rate, for example over a period of minutes, hours, or days.

The present invention further embodies imbibition as another method of treating seed with the pesticide. For example, plant seed can be combined for a period of time with a solution comprising from about 1% by weight to about 75% by weight of the pesticide in a solvent such as water. Preferably the concentration of the solution is from about 5% by weight to about 50% by weight, more preferably from about 10% by weight to about 25% by weight. During the period that the seed is combined with the solution, the seed takes up (imbibes) a portion of the pesticide. Optionally, the mixture of plant seed and solution can be agitated, for example by shaking, rolling, tumbling, or other means. After imbibition, the seed can be separated from the solution and optionally dried, for example by patting or air drying.

In yet another embodiment, a powdered pesticide can be mixed directly with seed. Optionally, a sticking agent can be used to adhere the powder to the seed surface. For example, a quantity of seed can be mixed with a sticking agent and optionally agitated to encourage uniform coating of the seed with the sticking agent. The seed coated with the sticking agent can then be mixed with the powdered pesticide. The mixture can be agitated, for example by tumbling, to encourage contact of the sticking agent with the powdered pesticide, thereby causing the powdered pesticide to stick to the seed.

The present invention also provides a transgenic corn seed that has been treated with a pesticide by the method described above.

The treated seeds of the present invention can be used for the propagation of corn plants in the same manner as conventional treated corn seed. The treated seeds can be stored, handled, sowed and tilled in the same manner as any other pesticide treated seed. Appropriate safety measures should be taken to limit contact of the treated seed with humans, food or feed materials, water and birds and wild or domestic animals.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. In the examples all percentages are given on a weight basis unless otherwise indicated.

EXAMPLE 1

Production of corn seed having a transgenic event effective against corn rootworm and treatment of such seed with imidacloprid (Gaucho®) and tefluthrin (Raze®).

Corn seeds were prepared to express *Bacillus thuringiensis* endotoxin Cry3Bb.11231 or Cry3Bb.11098 by the methods described for these respective events in WO 99/31248.

Corn seeds of the same hybrid species, with and without the respective transgenic events, were treated with either imidacloprid (available as GAUCHO® from Bayer Corp.) or tefluthrin (available as RAZE® from Wilbur-Ellis Co., Great Falls, Mont.; Walla Walla, Wash.) as follows. A seed treatment formulation of the desired pesticide was prepared by mixing a measured amount in water as a carrier and applying the formulation for one minute at room temperature to a measured weight of corn seed in a rotostatic seed treater. The respective weights of the pesticide preparation and the corn seed were calculated to provide the desired rate of treatment of pesticide on the seed. The pesticide was mixed into sufficient water to permit efficient distribution of the formulation to all of the seeds in the batch while minimizing loss of treatment formulation due to lack of uptake of the formulation by the seeds. Treated seeds were allowed to sit uncapped for at least four hours before planting.

When the seeds were treated with imidacloprid, a sufficient amount of Gaucho® 600 FS (containing 48.7% by weight imidacloprid; available from the Gustafson LLC) was thoroughly mixed into water to form a seed treatment formulation, and the formulation was applied to a weight of corn seed to provide treatment levels of 300 grams imidacloprid per 100 kg of seed (0.75 mg imidacloprid/kernel), or 400 grams imidacloprid per 100 kg of seed (1.0 mg imidacloprid/kernel).

When the seeds were treated with tefluthrin, a sufficient amount of Raze® 2.5 FS (containing 26.8% by weight tefluthrin; available from Wilbur-Ellis Co.,) was thoroughly mixed into water to form a seed treatment formulation, and the formulation was applied to a weight of corn seed to provide treatment levels of 300 grams active tefluthrin per 100 kg of seed (0.75 mg tefluthrin/kernel).

EXAMPLE 2

Field trials for the determination of efficacy of transgenic event Cry3Bb. 11231 in corn seed in combination with corn root worm pesticide seed treatments against western and northern corn rootworm.

Field trials were run in accordance with pertinent protocols and in conformance with USDA notification requirements. The purpose of the trials was to determine the efficacy of transgenic event Cry3Bb.11231 in corn seed in combination with corn root worm seed treatments against western and northern corn root worm.

For each growing site that was selected, the plot design included the following:

| | |
|---|---|
| Row spacing: | 30 inches |
| Plot size: | 4 rows × 20 |
| Plant density: | 2.0 seed/foot |
| Hybrid used: | LH198 × LH185 or RX670 |
| Replicates: | 4 |
| Design: | Randomized complete block |
| Locations: | 4 |
| Larvae source: | natural infestations supplemented by artificial infestation of corn rootworm eggs at 400 eggs/ft (growth stage V2) |

The following seed treatment combinations were used for each growing area:

| No. | Corn Seed Type | Pesticide and amount (grams AI/100 kg seed or mg ai/kernel |
|---|---|---|
| 1 | Isohybrid | None, other than low levels for wire worm protection |
| 2 | Cry3Bb.11231 | None, other than low levels for wire worm protection |
| 3 | Cry3Bb.11231 | Gaucho ® 600 FS @ 300 gm AI/100 kg or .75 mg AI/kernel |
| 4 | Cry3Bb.11231 | Gaucho ® 600 FS @ 400 gm AI/100 kg or 1.0 mg AI/kernel |
| 5 | Cry3Bb.11231 | Raze ® 2.5 FS @ 300 gm AI/100 kg or .75 mg AI/kernel |
| 6 | Isohybrid | Force ® 3G @ 0.014 gm AI/m, or 0.15 oz AI/1000 ft row, applied as a 5″ band on the soil surface at the time of planting. |
| 7 | Isohybrid | Lorsban ® 15G (chlorpyrifos; available from DowElanco) @ 0.11 gm AI/m, or 1.2 oz AI/1000 ft row, applied as a 5″ band on the soil surface at the time of planting. |

All seed treatments with pesticides were carried out as described in Example 1. In seed treatment number 1 and 2, Gaucho® was used for wire worm protection, but at levels sufficiently low that it would be expected to have no effect on corn rootworms (i.e., at a treatment level of about 60 gm of active/100 kg seed or 0.16 mg active/kernel), otherwise, seed receiving treatment number 2 had only transgenic event Cry3Bb.11231 and no pesticide treatment that would be expected to be effective against corn rootworm.

For seeds having treatments numbered 3 through 5, the pesticides were applied by the methods described in Example 1. For seeds having treatment numbers 6 and 7, commercially available Force® 3G and Lorsban® 15G were applied to the soil in a 5″ band at the time of sowing. The levels of application are as shown and are within the ranges recommended for standard commercial practice.

Corn seeds to be tested were planted and grown at four different locations across four Midwestern states in the United States corn belt according to the protocol described above.

The determination of damage by corn rootworm was made according to the following protocol. At stage V4–V6, an evaluation of early stand was made by counting the number of plants per acre. At stage VT-R1, an evaluation of corn rootworm damage was carried out by methods that are well known in the industry, and damage by corn rootworm was reported according to the Iowa 1–6 rating system. In that system, the root systems of 10 corn plants per plot are recovered and scored using the 1–6 rating scale, where: 1=no injury or only a few minor feeding scars, 2=feeding injury evident, but no roots eaten back to 1½ inches of the plant, 3=at least one root eaten off to within 1½ inches of the plant, but never an entire node of roots destroyed, 4=one node of roots eaten back to within 1½ inches of the plant, 5=two nodes (circles) of roots eaten back to within 1½ inches of the plant, 6=three nodes (circles) of roots eaten back to within 1½ inches of the plant.

Table 1(A). Corn rootworm damage to isohybrid corn plants having conventional surface banding treatments and corn plants having transgenic event Cry3Bb.11231 alone and in combination with seed treatment with selected pesticides at four growing locations.

| SEED NO. | SITE A | SITE B | SITE C | SITE D | MEANS ACROSS LOCATIONS |
|---|---|---|---|---|---|
| 1 | 4.3 | 4.0 | 4.0 | 4.2 | 4.1 |
| 2 | 2.5 | 2.4 | 2.2 | 2.0 | 2.3 |
| 3 | 2.1 | 2.3 | 2.5 | 1.9 | 2.2 |
| 4 | 1.8 | 2.3 | 2.2 | 1.8 | 2.0 |
| 5 | 2.3 | 2.3 | 2.6 | 1.8 | 2.2 |
| 6 | 2.7 | 2.1 | 2.6 | 1.9 | 2.3 |
| 7 | 3.3 | 2.4 | 2.5 | 1.8 | 2.5 |

From the data of Table 1 (A), it can be seen that transgenic seeds that were treated with either imidacloprid or tefluthrin at any level were more resistant to corn rootworm damage than the transgenic seeds without such pesticide treatment. Moreover, all combination treatments (of transgenic event plus pesticide treatment) were more efficacious that conventional surface banding with either FORCE® or LORSBAN®.

Therefore, it can be concluded that the treatment of a corn seed having a transgenic event with either imidacloprid or tefluthrin provides improved resistance over that provided by either the transgenic event alone, or isohybrid seed that has also received a standard pesticide surface banding treatment at planting.

EXAMPLE 3

Field trials for the determination of efficacy of transgenic event Cry3Bb.11231 in corn seed in combination with imidacloprid seed treatments against western and northern corn rootworm A field trial was run in accordance with pertinent protocols and in conformance with USDA notification requirements. The purpose of the trial was to determine the efficacy of transgenic event Cry3Bb.11231 in corn seed in combination with corn rootworm seed treatments using imidacloprid.

For each growing site that was selected, the plot design included the following:

| | |
|---|---|
| Row spacing: | 30 inches |
| Plot size: | 4 rows × 20 |
| Plant density: | 2.0 seed/foot |
| Hybrid used: | LH198 × LH185 or RX670 |
| Replicates: | 4 |
| Design: | Randomized complete block |
| Locations: | 4 |
| Larvae source: | natural infestations supplemented by artificial infestation of corn rootworm eggs at 400 eggs/ft (growth stage V2) |

The following seed treatment combinations were used for each growing area:

| No. | Corn Seed Type | Pesticide and amount (grams AI/100 kg seed or mg ai/kernel) |
|---|---|---|
| 1 | Isohybrid | None, other than low levels for wire worm protection |
| 2 | Cry3Bb.11231 | None, other than low levels for wire worm protection |
| 3 | Cry3Bb.11231 | Gaucho ® 600 FS @ 300 gm AI/100 kg or .75 mg AI/kernel |
| 4 | Cry3Bb.11231 | Gaucho ® 600 FS @ 400 gm AI/100 kg or 1.0 mg AI/kernel |
| 5 | Cry3Bb.11231 | Raze ® 2.5 FS @ 300 gm AI/100 kg or .75 mg AI/kernel |
| 6 | Isohybrid | Force ® 3G @ 0.014 gm AI/m, or 0.15 oz AI/1000 ft row, applied as a 5" band on the soil surface at the time of planting. |
| 7 | Isohybrid | Lorsban ® 15G (chlorpyrifos; available from DowElanco) @ 0.11 gm AI/m, or 1.2 oz AI/1000 ft row, applied as a 5" band on the soil surface at the time of planting. |

All seed treatments with pesticides were carried out as described in Example 1. In seed treatment number 1 and 2, Gaucho® was used for wire worm protection, but at levels sufficiently low that it would be expected to have no effect on corn rootworms (i.e., at a treatment level of about 60 gm of active/100 kg seed or 0.16 mg active/kernel), otherwise, seed receiving treatment number 2 had only transgenic event Cry3Bb.11231 and no pesticide treatment that would be expected to be effective against corn rootworm.

For seeds having treatments numbered 3 through 5, the pesticides were applied by the methods described in Example 1. For seeds having treatment numbers 6 and 7, commercially available Force® 3G and Lorsban® 15G were applied to the soil in a 5" band at the time of sowing. The levels of application are as shown and are within the ranges recommended for standard commercial practice.

Corn seeds to be tested were planted and grown at four different locations across several Midwestern states in the United States corn belt according to the protocol described above.

The determination of damage by corn root worm was made according to the protocol described in Example 2.

Table 2(A). Corn rootworm damage to isohybrid corn plants and corn plants having transgenic event Cry3Bb.11231 alone and in combination with seed treatment with imidacloprid pesticide at different growing locations.

| TREATMENT | CORN ROOTWORM DAMAGE IN EACH IOWA CLASS (IOWA 1–6 SCALE) | | | | | | GRAND TOTAL | PERCENT OF CONTROL |
|---|---|---|---|---|---|---|---|---|
| | 1 | 2 | 3 | 4 | 5 | 6 | | |
| Isohybrid | 0 | 3 | 16 | 36 | 21 | 4 | 80 | 100 |
| Cry3Bb.11231 | 5 | 51 | 23 | 1 | 0 | 0 | 80 | 31.2 |
| Imidacloprid @ 400 g/100 kg of seed | 3 | 15 | 36 | 21 | 5 | 0 | 80 | 80.5 |
| Cry3Bb.11231 with Imidacloprid @ 400 gm/100 kg of seed | 13 | 53 | 14 | 0 | 0 | 0 | 80 | 18.2 |
| FORCE ® 3G surface band at planting | 3 | 58 | 34 | 3 | 0 | 0 | 98 | 39.2 |
| LORSBAN ® 15G surface band at planting | 6 | 39 | 38 | 16 | 1 | 0 | 100 | 57.1 |

Notes: a. Data for the isohybrid control was taken as the same as determined for a related protocol that was carried out in an adjoining plot.

The data showed that both the transgenic event alone and seed treatment with imidacloprid alone provided some level of protection against corn rootworm damage above the untreated isohybrid control. At higher levels of damage (i.e., damage levels 4–6), corn having the transgenic event suffered 4.7% of the damage of the non-transgenic control. Since 4.7% would be considered to be about 5%, the Cry3Bb.11231 event was considered to be within a preferred effectiveness range of about 5% to about 50% of the damage of the non-transgenic control.

Imidacloprid seed treatment alone at 400 gm/100 kg was effective against corn rootworm damage, but the effectiveness of imidacloprid was lower than the effectiveness of the transgenic event alone. The combination of treatment with imidacloprid of the transgenic seed was more effective against rootworm damage than the pesticide treatment alone or the transgenic event alone. Moreover, the combination of Cry3Bb.11231 with imidacloprid at 400 gm/100 kg of seed provided better protection than the commercial standard treatment of either FORCE® or LORSBAN® applied as a surface band at planting.

The advantages of the present treatment of transgenic seed with imidacloprid include the simplification of planting, by removing the requirement for separate application of the pesticide. Furthermore, planting is easier and safer, since the planter does not have to handle a concentrated pesticide.

The combination of imidacloprid seed treatment with corn seed having a Cry3Bb.11231 transgenic event was tested for possible synergy at a level of rootworm damage of 3–6. In the first test, shown in Table 2(A), the percentage of test plants having damage levels of from 3 to 6, on the Iowa 1–6 Scale, was determined for the control and for seeds treated with the pesticide at two levels, and for seeds having the transgenic event, alone and in combination. The following formula was then used to calculate a "synergy threshold":

(% of control Cry3Bb.11231)*(% of control imidacloprid treatment)/100.

This threshold was compared against the percent of control for the treatment combination (i.e., Cry3Bb.11231 with imidacloprid @ 400 gm/100 kg). If the treatment combination percent of control was below the threshold, then it was concluded that there was synergy. If the treatment combination percent of control was above the threshold, then it was concluded that synergy was not demonstrated for that combination.

It was believed that the measurement of rootworm damage at higher damage levels (i.e., levels 3–6) is a useful indicator that correlates with subsequent yield loss due to such damage. The reason for this is that rootworm damage at levels 1 and 2 seldom causes corn plants to fall over and lodge, and such minimal root loss is not believed to reduce the number or weight of kernels per ear. However, root damage at levels of 3 and above increasingly causes lodging and loss of yield. Therefore, it is believed that the summed damage levels of 3–6 (and in some cases, 4–6 and 5 and 6), provides a useful indication of the effect of corn rootworm damage on subsequent corn yield.

Table 2(B). Efficacy of seed treatment with imidacloprid alone and in combination with corn transgenic event Cry3Bb.11231 against corn rootworm damage at levels 3–6 on the Iowa 1–6 Scale.

| TREATMENT | NUMBER OF PLANTS HAVING 3–6 DAMAGE LEVEL | PERCENT OF CONTROL | THRESHOLD SYNERGY |
|---|---|---|---|
| Untreated Control | 96.1 | 100 | — |
| Cry3Bb.11231 | 40 | 31.2 | — |
| Imidacloprid @ 400 gm/100 kg | 71.7 | 80.5 | — |
| Cry3Bb.11231 with imidacloprid @ 400 gm/100 kg | 24 | 18.2 | 25.1 |
| FORCE 3G as surface band | 40.7 | 39.2 | — |

-continued

| TREATMENT | NUMBER OF PLANTS HAVING 3–6 DAMAGE LEVEL | PERCENT OF CONTROL | THRESHOLD SYNERGY |
|---|---|---|---|
| LORSBAN 15G as surface band | 60.8 | 57.1 | — |

This analysis indicated that the combination of the corn Cry3Bb.11231 transgenic event with seed treatment with imidacloprid at 400 gm/100 kg was synergistic and unexpectedly efficacious against corn rootworm damage at the 3–6 level. Accordingly, it was concluded that the combination of the transgenic event with the imidacloprid seed treatment provided significant advantages over the use of either method alone, and that such protection was unexpectedly superior in efficacy against severe damage by corn rootworm.

It was also believed to be noteworthy that the combination of imidacloprid and transgenic event provided protection against severe corn rootworm damage at levels that were far better than that provided by either FORCE® or LORSBAN® applied as surface bands.

EXAMPLE 4

Field trials for the determination of efficacy of transgenic event Cry3Bb.11231 in corn seed in combination with tefluthrin pesticide seed treatments against western and northern corn rootworm.

A field trial for the determination of efficacy of the combination of transgenic event Cry3Bb.11231 in corn seed with tefluthrin (available as RAZE® from Wilbur-Ellis Company) could be carried out according to the same protocol as described in Example 3, except that tefluthrin would be substituted for imidacloprid in each case where imidacloprid was used at levels expected to be effective against corn rootworm (e.g., at levels of higher than 60 gm/100 kg seed). If desirable, it would be permissible to continue to use imidacloprid at levels of 60 gm/100 kg, or less, for wireworm protection.

It would be expected that the combination of tefluthrin seed treatment with a transgenic event in corn seed having effectiveness against corn rootworm would provide synergistic protection similar to that shown in Example 3 for the combination of imidacloprid and Cry3Bb.11231.

The discussion of the references herein is intended merely to summarize the assertions made by their authors and no admission is made that any reference constitutes prior art. Applicants reserve the right to challenge the accuracy and pertinence of the cited references.

In view of the above, it will be seen that the several advantages of the invention are achieved and other advantageous results attained.

As various changes could be made in the above methods and compositions without departing from the scope of the invention, it is intended that all matter contained in the above description shall be interpreted as illustrative and not in a limiting sense.

What is claimed is:

1. A method for protecting a transgenic corn plant against feeding damage by one or more pests, the method comprising
   providing a seed for the transgenic corn plant, wherein the seed comprises a transgenic event having activity against at least one of the one or more pests; and
   treating the seed with an effective amount of a pesticide other than thiamethoxam or clothianidin which, in combination with the transgenic event, is effective to protect a corn plant which grows from the corn seed against feeding damage by at least one of the one or more pests to a degree greater than would be expected due to either the pesticide or the transgenic event alone.

2. The method according to claim 1 wherein the transgenic event comprises the ability to express a Cry 3 protein.

3. The method according to claim 2 wherein the transgenic event comprises the ability to express a Cry3* protein.

4. The method according to claim 3 wherein the Cry3* protein is a Cry3B* protein.

5. The method according to claim 4 wherein the Cry 3B* protein is selected from the group consisting of Cry3Bb.11230, Cry3Bb.11231, Cry3Bb.11232, Cry3Bb.11233, Cry3Bb.11234, Cry3Bb.11235, Cry3Bb.11236, Cry3Bb.11237, Cry3Bb.11238, Cry3Bb.11239, Cry3Bb.11241, Cry3Bb.11242, and Cry3Bb.11098.

6. The method according to claim 5 wherein the Cry 3B* protein is Cry3Bb.11231.

7. The method according to claim 5 wherein the Cry3B* protein is Cry3Bb.11098.

8. The method according to claim 2 wherein the transgenic event is capable of reducing the damage caused by corn rootworm so that the damage to the transgenic corn is within the range of from about 5% to about 50% of the damage to non-transgenic corn under the same conditions, when such damage is expressed as the percent of the corn plants having a score of 4–6 as measured by Iowa Corn Rootworm 1–6 Scale.

9. The method according to claim 8 wherein the transgenic event is capable of reducing the damage caused by the corn rootworm so that the damage to the transgenic corn is within the range of from about 10% to about 40% of the damage to non-transgenic corn under the same conditions, when such damage is expressed as the percent of the corn plants having a score of 4–6 as measured by the Iowa Corn Rootworm 1–6 Scale.

10. The method according to claim 9 wherein the transgenic event is capable of reducing the damage caused by the corn rootworm so that the damage to the transgenic corn is within the range of about 15% to about 30% of the damage to the non-transgenic corn under the same conditions, when such damage is expressed as the percent of the corn plants having a score of 4–6 as measured by the Iowa Corn Rootworm 1–6 Scale.

11. The method according to claim 10 wherein the transgenic event is capable of reducing the damage caused by the corn rootworm so that the damage to the transgenic corn is within the range of about 20% to about 30% of the damage to the non-transgenic corn under the same conditions, when such damage is expressed as the percent of the corn plants having a score of 4–6 as measured by the Iowa Corn Rootworm 1–6 Scale.

12. The method according to claim 2 wherein the seed having the ability to express the Cry 3 protein also has the ability to express at least one other insecticidal protein that is different from a Cry 3 protein.

13. The method according to claim 2 wherein the seed having the ability to express the Cry 3 protein also has a transgenic event that provides herbicide tolerance.

14. The method according to claim 13 wherein the transgenic event that provides the herbicide tolerance against glyphosate.

15. The method according to claim 2 wherein the transgenic event has activity against an insect.

16. The method according to claim 15 wherein the insect is selected from the group consisting of members of the orders of Lepidoptera, Coleoptera and Hemiptera.

17. The method according to claim 16 wherein the insect is the Coleopteran insect.

18. The method according to claim 17 wherein the insect is the Diabrotica spp.

19. The method according to claim 18 wherein the insect comprises at least one member selected from the group consisting of *Diabrotica virgifera, Diabrotica barberi* and *Diabrotica undecimpunctata*.

20. The method according to claim 2 wherein the pesticide is selected from the group consisting of insecticides, acaricides, nematocides, fungicides, bactericides, and herbicides.

21. The method according to claim 20 wherein the pesticide is the insecticide.

22. The method according to claim 21 wherein the pesticide is selected from the group consisting of pyrethrins, synthetic pyrethroids, oxadiazines, chloronicotinyls, nitroguanidine insecticides, triazoles, organophosphates, pyrrols, pyrazoles, diacylhydrazines, biological/fermentation products, and carbamates.

23. The method according to claim 22 wherein the pesticide is selected from the group consisting of 2-allyl-4-hydroxy-3-methyl-2-cyclopenten-1-one ester of 2,2-dimethyl-3-(2methyl propenyl)-cyclopropane carboxylic acid, and/or (2-methyl-1-propenyl)-2-methoxy-4-oxo-3-(2 propenyl)-2-cyclopenten-1-yl ester, (s)-cyano(3-phenoxyphenyl)methyl 4-chloro alpha (I-methylethyl) benzeneacetate (fenvalerate), (S)-cyano (3-phenoxyphenyl) methyl (S)-4-chloro-alpha-(1-methylethyl) benzeneacetate (esfenvalerate), (3-phenoxyphenyl)-methyl(+)cis-trans-3-(2,2-dichoroethenyl)-2,2-dimethylcyclopropanecarboxylate (permethrin), (±) alpha-cyano-(3-phenoxyphenyl) methyl (+)-cis, trans-3-(2,2-dichloroethenyl)-2,2-dimethyl-cyclopropane carboxylate (cypermethrin), beta-cypermethrin, theta cypermethrin, S-cyano (3-phenoxyphenyl) methyl (±) cis/trans 3-(2,2-dichloroethenyl) 2,2 dimethylcyclopropane carboxylate (zeta-cypermethrin), (s)-alpha-cyano-3-phenoxybenzyl (IR, 3R)-3-(2,2-dibromovinyl)-2,2-dimethylcyclopropanecarboxylate (deltamethrin), alpha-cyano-3-phenoxybenzyl 2,2,3,3,-tetramethyl cyclopropoanecarboxylate (fenpropathrin), (RS)-alpha-cyano-3-phenoxybenzyl(R)-2-[2-chloro-4-(trifluoromethyl)anilino]-3-methylbutanoate (tau-fluvalinate), (2,3,5,6-tetrafluoro-4-methylphenyl)-methyl-(1 alpha, 3 alpha)-(Z)-(±)-3-(2-chloro-3,3,3-trifluoro-1-propenyl)-2,2-dimethylcyclopropanecarboxylate (tefluthrin), (±)-cyano (3-phenoxyphenyl) methyl (±)-4-(difluoromethoxy)-alpha-(1-methyl ethyl) benzeneacetate (flucythrinate), cyano(4-fluoro-3-phenoxyphenyl)methyl 3-[2-chloro-2-(4-chlorophenyl)ethenyl]-2,2-dimethylcyclopropanecarboxylate (flumethrin), cyano(4-fluoro-3-phenoxyphenyl) methyl 3-(2,2-dichloroethenyl)-2, 2-dimethyl-cyclopropanedarboxylate (cyfluthrin), beta cyfluthrin, transfluthrin, (S)-alpha-cyano-3-phenoxybenzyl (Z)-(IR-cis)-2,2-dimethyl-3-[2-(2,2,2-trifluoro-trifluoromethyl-ethoxycarbonyl)vinyl]cyclopropane carboxylate (acrinathrin), (IR cis) S and (IS cis) R enantiomer isomer pair of alpha-cyano-3-phenoxybenzyl-3-(2,2-dichlorovinyl)-2,2-dimethylcyclopropane carboxylate (alpha-cypermethrin), [IR,3S)3(1'RS)(1',2',2',2'-tetrabromoethyl)]-2,2-dimethyl cyclopropanecarboxylic acid (s)-alpha-cyano-3-phenoxybenzyl ester (tralomethrin), cyano-(3-phenoxyphenyl) methyl 2,2-dichloro-1-(4-ethoxyphenyl)cyclopropane carboxylate (cycloprothrin), [1α, 3α(Z)]-(±)-cyano-(3-phenoxyphenyl)methyl 3-(2-chloro-3,3,3-trifluoro-1-propenyl)-2,2-cimethylcyclopropanecarboxylate (cyhalothrin), [1 alpha (s), 3 alpha(z)]-cyano(3-phenoxyphenyl) methyl-3-(2-chloro-3,3,3-trifluoro-1-propenyl)-2,2-dimethylcyclopropane carboxylate (lambda cyhalothrin), (2-methyl [1,1'-biphenyl]-3-yl) methyl 3-(2-chloro-3,3,3-trifluoro-1-propenyl)-2,2-dimethyl-cyclopropanecarboxylate (bifenthrin), 5-1-benzyl-3-furylmethyl-d-cis(1R, 3S,E)2,2-dimethyl-3-(2-oxo ,-2,2,4,5 tetrahydro thiophenylidenemethyl)cyclopropane carboxylate (kadethrin), [5-(phenyl methyl)-3-furanyl]-3-furanyl 2,2-dimethyl-3-(2-methyl-1-propenyl) cyclopropane carboxylate (resmethrin). (1R-trans)-[5-(phenylmethyl)-3-furanyl]methyl 2,2-dimethyl-3-(2-methyl-1-propenyl) cyclopropanecarboxylate (bioresmethrin), 3,4,5,6-tetra hydrophthalimidomethyl-(IRS)-cis-trans-chrysanthemate (tetramethrin), 3-phenoxybenzyl-d,I-cis,trans 2,2-dimethyl-3-(2-methylpropenyl) cyclopropane carboxylate (phenothrin), empenthrin, cyphenothrin, prallethrin, imiprothrin, (RS)-3-allyl-2-methyl-4-oxcyclopent-2-enyl-(1A,3R; 1R,3S)-2,2-dimethyl-3-(2-methylprop-1-enyl) cyclopropane carboxylate (allethrin), bioallethrin, ZXI8901, 5-(2-chloropyrid-5-ylmethyl)-3-methyl-4-nitroiminoperhydro-1,3,5-oxadiazine, 3-methyl-4-nitroimino-5-(1-oxido-3-pyridinomethyl) perhydro-1,3,5-oxadiazine, 5-(2-chloro-1-oxido-5-pyridiniomethyl)-3-methyl-4-nitroiminoperhydro-1,3,5-oxidiazine, 3-methyl-5-(2-methylpyrid-5-ylmethyl)-4-nitroiminoperhydro-1,3,5-oxadiazine, acetamiprid ((E)-N-[(6-chloro-3-pyridinyl) methyl]-N'-cyano-N-methyleneimidamide), imidacloprid (1-[(6-chloro-3-pyridinyl)methol]-N-nitro-2-imidazolidinimime), nitenpyram (N-[(6-chloro-3-pyridinyl) methyl]-N-ethyl-N'-methyl-2-nitro-1,1-ethenediamine), chlorfenapyr (4-bromo-2-(4-chlorophenyl)-1-ethoxymethyl-5-trifluoromethylpyrrole-3-carbonitrile), fenpyroximate ((E)-1,1-dimethylethyl-4[[[[(1,3-dimethyl-5-phenoxy-1H-pyrazole-4-yl)methylene]amino]oxy]methyl] benzoate), tebufenpyrad (4-chloro-N[[4-1,1-dimethylethyl) phenyl]methyl]-3-ethyl-1-methyl-1H-pyrazole-5-carboxamide); phenyl pyrazoles including fipronil (5-amino-[2,6-dichloro-4-(trifluoromethyl)phenyl]-4-[(1R, S)-(trifluoromethyl)sulfinyl]-1H-pyrazole-3-carbonitrile), halofenozide (4-chlorobenzoate-2-benzoyl-2-(1,1-dimethylethyl)-hydrazide), methoxyfenozide (RH-2485, N-tert-butyl-N'-(3-methoxy-o-toluoyl)-3,5-xylohydrazide), tebufenozide (3,5-dimethylbenzoic acid 1-(1,1-dimethylethyl)-2,(4-ethylbenzoyl)hydrazide), amitrole, triazamate, avermectin (abamectin), spinosad (XDE-105), acephate, chlorpyrifos, chlorpyrifos-methyl , diazinon, fenamiphos, malathion, aldicarb, carbaryl, carbofuran, oxamyl, and thiodicarb.

24. The method according to claim 22, wherein the pesticide comprises the oxadiazine.

25. The method according to claim 24, wherein the oxadizine comprises an insecticide selected from the group consisting of 5-(2-chloropyrid-5-ylmethyl)-3-methyl-4-nitroiminoperhydro-1,3,5-oxadiazine, 3-methyl-4-nitroimino-5-(1-oxido-3-pyridinomethyl) perhydro-1,3,5-oxadiazine, 5-(2-chloro-1-oxido-5-pyridiniomethyl)-3-methyl-4-nitroiminoperhydro-1,3,5-oxidiazine, and 3-methyl-5-(2-methylpyrid-5-ylmethyl)-4-nitroiminoperhydro-1,3,5-oxadiazine.

26. The method according to claim 20, wherein the pesticide comprises a chloronicotinyl insecticide.

27. The method according to claim 26, wherein the chloronicotinyl insecticide is selected from the group consisting of acetamiprid ((E)-N-[(6-chloro-3-pyridinyl) methyl]-N'-cyano-N-methyleneimidamide), imidacloprid (1-[(6-chloro-3-pyridinyl)methol]-N-nitro-2-imidazolidinimime), and nitenpyram (N-[(6-chloro-3-pyridinyl)methyl]-N-ethyl-N'-methyl-2-nitro-1,1-ethenediamine).

28. The method according to claim 20, wherein the pesticide comprises a nitroguanidine insecticide.

29. The method according to claim 20 wherein the pesticide is glyphosate.

30. The method according to claim 22 wherein the transgenic event comprises the ability to express the protein selected from the group consisting of Cry3Bb.11230, Cry3Bb.11231, Cry3Bb.11232, Cry3Bb.11233, Cry3Bb.11234, Cry3Bb.11235, Cry3Bb.11236, Cry3Bb.11237, Cry3Bb.11238, Cry3Bb.11239, Cry3Bb.11241, Cry3Bb.11242, and Cry3Bb.

31. The method according to claim 30 wherein the pesticide is selected from the group consisting of imidacloprid and tefluthrin.

32. The method according to claim 31 wherein the pesticide comprises the imidacloprid.

33. The method according to claim 32 wherein the transgenic event comprises the ability to express the Cry3Bb.11231 protein.

34. The method according to claim 32 wherein the transgenic event comprises the ability to express the Cry3Bb.11098 protein.

35. The method according to claim 31 wherein the pesticide is the tefluthrin.

36. The method according to claim 35 wherein the transgenic event comprises the ability to express the Cry3Bb.11231 protein.

37. The method according to claim 35 wherein the transgenic event comprises the ability to express the Cry3Bb.11098 protein.

38. The method of claim 22 wherein the effective amount of the pesticide is from at least about 10 grams to about 2000 grams of the pesticide active ingredient per 100 kilograms of the seed.

39. The method of claim 38 wherein the effective amount of the pesticide is from at least about 70 grams to about 1000 grams of the pesticide active ingredient per 100 kilograms of the seed.

40. The method of claim 39 wherein the effective amount of the pesticide is from at least about 100 grams to about 600 grams of the pesticide active ingredient per 100 kilograms of the seed.

41. The method of claim 40 wherein the effective amount of the pesticide is from at least about 200 grams to about 500 grams of the pesticide active ingredient per 100 kilograms of the seed.

42. A seed of a transgenic corn plant that provides increased resistance to the resulting corn plant against feeding damage by one or more pests, the seed comprising a transgenic event having activity against at least one of the one or more pests, wherein the seed has been treated with an effective amount of a pesticide other than thiamethoxam or clothianidin which, in combination with the transgenic event, is effective to protect the corn plant which grows from the corn seed against feeding damage by at least one of the one or more pests to a degree greater than would be expected due to either the pesticide or the transgenic event alone.

43. The seed of claim 42 wherein the transgenic event comprises a gene that encodes a Cry3 protein derived from *Bacillus thuringiensis*.

44. The seed of claim 43 wherein the transgenic event comprises a gene that encodes a Cry3Bb protein derived from *Bacillus thuringiensis*.

45. The seed of claim 43 wherein the transgenic event comprises a gene that encodes a Cry3Bb.11230, Cry3Bb.11231, Cry3Bb.11232, Cry3Bb.11233, Cry3Bb.11234, Cry3Bb.11235, Cry3Bb.11236, Cry3Bb.11237, Cry3Bb.11238, Cry3Bb.11239, Cry3Bb.11241, Cry3Bb.11242, or a Cry3Bb.11098 protein derived from *Bacillus thuringiensis*.

46. A transgenic corn seed that has been treated to protect a transgenic corn plant that grows from the seed against feeding damage by one or more pests by the method comprising:

providing the seed for the transgenic corn plant, wherein the seed comprises a transgenic event having activity against at least one of the one or more pests; and treating the seed with an effective amount of a pesticide other than thiamethoxam or clothianidin which, in combination with the transgenic event, is effective to protect the corn plant which grows from the corn seed against feeding damage by at least one of the one or more pests to a degree greater than would be expected due to either the pesticide or the transgenic event alone, wherein the pesticide is selected from the group consisting of pyrethrins, synthetic pyrethroids, oxadiazines, chloronicotinyls, nitroguanidine insecticides, triazoles, organophosphates, pyrrols, pyrazoles, diacylhydrazines, biological/fermentation products, and carbamates.

\* \* \* \* \*